United States Patent [19]

Sheldon et al.

[11] 4,123,451

[45] Oct. 31, 1978

[54] PREPARATION OF ESTERS

[75] Inventors: Roger A. Sheldon; Peter Been, both of Amsterdam, Netherlands

[73] Assignee: Shell Oil Company, Houston, Tex.

[21] Appl. No.: 765,188

[22] Filed: Feb. 3, 1977

[30] Foreign Application Priority Data

Mar. 1, 1976 [GB] United Kingdom ................ 8046/76

[51] Int. Cl.$^2$ ................ C07C 120/00; C07C 121/66; C07C 120/04
[52] U.S. Cl. ................................ 260/465 D
[58] Field of Search .................... 260/465 D

[56] References Cited

U.S. PATENT DOCUMENTS 3,835,176  9/1974  Matsuo et al. .................. 260/465 D

OTHER PUBLICATIONS

Zymalkowski et al., Arch. Pharmaz. Ber. Pharmaz. Ges. 62, Nr. 5, pp. 218–224 (1956).
Francis et al., J. Chem. Soc., 95, pp. 1403–1409 (1909).
Kinder et al., Arch. Pharm., 271, pp. 431–439 (1933).
Coronyn, J. Org. Chem., 14, pp. 1013–1022 (1949).
Fisher et al., J. Org. Chem., 24, pp. 1650–1654, (1959).

*Primary Examiner*—Dolph H. Torrence

[57] ABSTRACT

Certain carboxylic acid esters also containing a cyano group are prepared by reacting an acid halide, an aldehyde and a water-soluble cyanide in the presence of one or more water-immiscible (cyclo)alkane solvents.

13 Claims, No Drawings

PREPARATION OF ESTERS

BACKGROUND OF THE INVENTION

I. Field of the Invention

The invention relates to a process for the preparation of certain cyano-substituted carboxylic acid esters by reacting an acid halide, an aldehyde and a water-soluble cyanide.

II. Description of the Prior Art

According to U.S. Pat. No. 3,835,176, addition of substituted cyclopropanecarbonyl halides and m-substituted benzaldehydes, if necessary dissolved in an aprotic solvent, to an aqueous solution of sodium cyanide or potassium cyanide and stirring of the mixture obtained until no more conversion takes place, affords the desired esters. The experiment described in Example 4 of the above U.S. patent was conducted in the absence of a solvent, with an unsaturated aqueous solution of sodium cyanide, with a 20% molar excess of the cyclopropanecarbonyl halide (calculated on aldehyde) and at a temperature of 0° C.

Such a process has the disadvantages that the yield of the ester is relatively low and that keeping the temperature at 0° C and using the said molar excess are expensive.

The process according to the present invention obviates these disadvantages and affords the desired esters by using specific solvents.

SUMMARY OF THE INVENTION

The present invention is directed to a process for the preparation of an ester of formula I

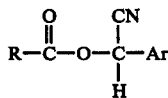

wherein R is an optionally substituted acyclic or saturated cyclic hydrocarbyl group and Ar is an optionally substituted aromatic group by contacting an aromatic aldehyde of the formula ArC(O)H and an acyl halide of the formula RC(O)Hal, in which formulas Ar and R have the same meanings as in Formula I and Hal is a halogen atom having an atomic number from 9 to 53, inclusive, with a water-soluble cyanide in the presence of one or more substantially water-immiscible (cyclo)alkane solvents.

Alkanes and cycloalkanes favour the shortest reaction times. Moreover, the esters of the formula I are thus obtained in a very high yield. Examples of suitable alkanes and cycloalkanes are those having up to 10 carbon atoms, preferably having 6 to 10 carbon atoms, such as n-heptane, n-octane, n-nonane, n-decane and their isomers, (for example, 2-methylpentane, and 2,4,4-trimethylpentane) and cyclohexane and methylcyclohexane. N-heptane and cyclohexane are very suitable solvents. Gasolines rich in alkanes are also very suitable, for example those with a boiling range at atmospheric pressure between 40° and 65° C, 60° and 80° C, or 80° and 110° C. The cyclo(alkanes) used according to the invention may contain up to 50% by weight of other substantially water-immiscible aprotic solvents, for example aromatic hydrocarbons such as 10% benzene or toluene or chlorinated hydrocarbons.

The process according to the present invention may be conducted starting from unsaturated or saturated aqueous solutions of water-soluble cyanide and in the latter case in the presence or absence of solid water-soluble cyanide. The use of solid water-soluble cyanide is covered in our co-pending U.S. patent application Ser. No. 765,184, filed Feb. 3, 1977 concurrently with the present application.

It has been found that when in a given case in which in successive comparable experiments less water and more solid water-soluble cyanide are applied (starting from a saturated aqueous solution of cyanide containing no solid-water-soluble cyanide constant) the reaction time can be kept shorter and shorter, passes a minimum and then becomes longer and longer until it has become as long as in the starting cases. The reaction time can usually be kept shortest when the starting molar ratio of the amount of water to the total amount of water-soluble cyanide is higher than 0.005, particularly higher than 0.01 and more particularly in the range of from 0.05 to 1. For comparison it may be stated that the molar ratios of water to sodium cyanide in a saturated aqueous solution of sodium cyanide at 10° C and 35° C are 5.7 and 3.3, respectively. Consequently, extremely small amounts of water are sufficient to obtain the shortest reaction times. Furthermore, the yield of the ester of the formula I is usually very high and in many cases quantitative or almost quantitative. In addition to the possibility of using short reaction times the use of solid water-soluble cyanide has a cost-saving effect, since smaller volumes of water can be handled.

The temperature at which the process is conducted is suitably above 0° C and is preferably in the range of from 10 to 50° C. Very good results are usually obtained at a temperature between 15° and 40° C. The process has an advantage that ambient temperatures are very suitable.

Another advantage of the process according to the present invention is that the molar ratio of the amount of (cyclo)aliphatic acyl halide to the amount of aromatic aldehyde can be kept so low that a molar excess of the halide is not or hardly not required. This molar ratio is preferably in the range of from 1.1 to 1.0 and is in particular equal to 1.0.

The molar ratio of the amount of water-soluble cyanide to the amount of aromatic aldehyde is suitably from 1.5 to 1.00 and preferably from 1.3 to 1.02. By "watersoluble cyanide" is meant a water-soluble salt of hydrogen cyanide. Of the water-soluble cyanides alkali-metal cyanides and alkaline-earth-metal cyanides are preferred. Sodium cyanide is particularly preferred, because it affords the esters of the formula I in the shortest reaction time.

The optionally substituted aromatic group Ar in the aromatic aldehyde of the formula ArC(O)H may be carbocyclic or heterocyclic. Examples of carbocyclic groups are phenyl, 1naphthyl, 2-naphthyl and 2-anthryl groups. Heterocyclic aromatic groups are derived from hetero-aromatic compounds which are defined as in Kirk-Orhmer, "Encyclopedia of Chemical Technology", Second Edition, Volume 2(1963), page 702: obtained by replacement of one or more carbon atoms of a carbocyclic aromatic compound by a hetero-atom - for example pyridine, pyrimidine, pyrazine, quinoline and isoquinoline - and also include those heterocyclic compounds having five-membered rings which show aromatic characteristics and are mentioned on page 703 of said volume, for example thiophene, pyrrole, furan, indole and benzothiophene. As an aromatic group an optionally substituted phenyl group is very suitable.

Examples of substituents are hydrocarbyl and hydrocarbyloxy groups. Very good results have been obtained with phenoxybenzaldehydes, particularly m-phenoxybenzaldehyde.

The group R in the formula RC(O)Hal may, for example, be an optionally substituted alkyl group. The alkyl group may be straight or branched. The alkyl group preferably has a tertiary or quaternary carbon atom bound to the group -C(O)Hal. Examples of such alkanoyl halides are 2-methylpropanoyl chloride, 2,2-dimethylpropanoyl chloride and 2-methylbutanoyl bromide. Very good results have been obtained with 2-methylbutanoyl chloride. The alkyl group may carry as substitutents, for example, hydrocarbyloxy or substituted phenyl groups, such as halophenyl or alkylphenyl. Very good results have been obtained with a 1-(4-chlorophenyl)-2-methylpropyl group. The expression "saturated cyclic hydrocarbyl group" in this patent application refers to cyclic hydrocarbyl groups in which the ring is saturated; this ring may carry substituents for example alkyl groups of 1 to 6 carbon atoms such as methyl, halogen atoms having atomic numbers of 9 to 35, inclusive, such as chlorine, bromine or fluorine and/or unsaturated side chains such as isobutenyl, dichlorovinyl or dibromovinyl. Examples of saturated cyclic hydrocarbyl groups are cyclopropyl, cyclobutyl and cyclohexyl groups. Very good results have been obtained with optionally substituted cyclopropanecarbonyl halides, particularly with 2,2,3,3-tetramethylcyclopropanecarbonyl halides and 2-(2,2-dichlorovinyl)-3,3-dimethylcyclopropanecarbonyl halides.

Hal preferably represents a chlorine or bromine atom and particularly a chlorine atom.

The process according to the invention may be carried out by gradual addition of the acyl halide to a vigorously agitated, e.g. stirred, mixture of the other starting compounds (particularly recommended when R in the formula RC(O)Hal represents a 2,2,3,3-tetramethylcyclopropyl group) and often by placing together the total amounts of the starting compounds and vigorous agitating e.g., stirring, of the mixture thus formed, which is particularly recommended when R represents a 1-(4-chlorophenyl)-2-methylpropyl, a isopropyl or a 2-(2,2-dichlorovinyl)-3,3-dimethylcyclopropyl group.

The process is of particular interest to prepare pesticidally active esters, for example: when the aromatic aldehyde is 3-phenoxybenzaldehyde and the acyl halide is a aralkyl halide such as 2-(4-chlorophenyl)-3-methylbutanoyl chloride, or a substituted-cyclopropanecarbonyl halide such as 2,2,3,3-tetramethylcyclopropanecarbonyl chloride or 2-(2,2-dichlorovinyl)-3,3-dimethylcyclopropanecarbonyl chloride, the esters then formed are α-cyano-3-phenoxybenzyl 2,2,3,3-tetramethylcyclopropanecarboxylate and α-cyano-3-phenoxybenzyl 2-(2,2-dichlorovinyl)-3,3-dimethylcyclopropanecarboxylate, respectively, all of which are pesticidally active compounds as disclosed in Belgian Pat. No. 801,946, U.S. Pat. No. 3,835,176 and Netherlands publication 7,307,130, respectively.

EXAMPLES

The examples further illustrate the invention. All experiments were conducted at a temperature of 23° C, unless otherwise stated. The sodium cyanide used consisted of particles having a largest dimension of 0.5 mm and contained 0.44% by weight of water. The molar ratio of water to sodium cyanide has been calculated taking into account the water present in the sodium cyanide and the water added, if any. For comparison it may be stated that the molar ratio of water to sodium cyanide in a saturated aqueous solution of sodium cyanide having a temperature of 23° C is 4.1. The reaction mixtures were stirred vigorously and analysed by gas-liquid chromatography to determine the yield of the ester formed. Reaction mixtures were filtered to remove precipitated sodium chloride and sodium cyanide, if any, and drying of solutions was carred out over anhydrous sodium sulphate. Flashing of the solvent took place in a film evaporator at a pressure of 15 mm Hg. All yields are calculated on starting aromatic aldehyde.

EXAMPLE I.

Preparation of α-cyano-3-phenoxybenzyl 2-(4-chlorophenyl)-3-methylbutanoate

A 50 ml round-bottomed flask equipped with a magnetic stirrer was charged with 10 mmol of 3-phenoxybenzaldehyde, 10 mmol of 2-(4-chlorophenyl)-3-methylbutanoyl chloride, 12 mmol of sodium cyanide, 1.00 ml of water and 20 ml of n-heptane. The molar ratio of water to sodium cyanide was 4.64, all NaCN being dissolved. The reaction mixture was stirred and analysed. The yield of the ester wanted is presented in Table I (experiment 1).

Experiment 2 is a repetition of experiment 1, the difference being that 20 ml of toluene was used instead of 20 ml of n-heptane and 10.5 mmol of the acyl halide instead of 10 mmol. The yield of the desired ester is presented in Table I.

TABLE I

| Experiment no. | Solvent | Reaction time, h | Yield of ester, % |
|---|---|---|---|
| 1 | n-heptane | 3 | 86 |
|   |   | 18 | more than 99 |
| 2 | toluene[1] | 3 | 41 |
|   |   | 24 | 87 |
|   |   | 85 | 95 |

[1]not according to the invention

Comparisons of the yields show that n-heptane is the best solvent.

EXAMPLE 2

Preparation of α-cyano-3-phenoxybenzyl 2-(4-chlorophenyl)-3-methylbutanoate in the presence of various solvents and solid cyanide A 50 ml round-bottomed flask equipped with a magnetic stirrer was charged with 10 mmol of 3-phenoxybenzaldehyde, 10.0 or 10.5 mmol of 2-(4-chlorophenyl)-3-methylbutanoyl chloride, 12 mmol of sodium cyanide, 0.02 ml of water and 20 ml of an aprotic solvent. The molar ratio of water to sodium cyanide was 0.105, solid NaCN being present. The reaction mixture was stirred and analyzed. Thirteen experiments were conducted in this manner, see Table II, stating which solvents were used. Experiments 2, 3, 4, 8 and 9 were conducted with 10.0 and the other experiments with 10.5 mmol of 2-(4-chlorophenyl)-3-methylbutanoyl chloride. The petroleum ether used in experiment 3 consisted of 97% by weight of alkanes and 3% by weight of benzene and had a boiling range at atmospheric pressure between 62° and 82° C. The ester remained in solution during the reaction in experiments 3 and 4. The reaction mixture obtained in experiment 4 was filtered and the cyclohexane was flashed from the filtrate to give the ester wanted as a colourless oil in quantitative yield. Table II also presents the yields of the desired ester. Comparison of the yields shows that the alkanes and cyclohexane are the best solvents.

TABLE II

| Experiment no. | Solvent | Reaction time, h | Yield of ester, % |
|---|---|---|---|
| 1 | n-heptane | 1.0 | more than 99 |
| 2 | 2,4,4-trimethyl-pentane | 1 | 92 |
|   |   | 2 | 99 |
| 3 | petroleum ether | 1 | 91 |
|   |   | 2 | 99 |
| 4 | cyclohexane | 1 | 80 |
|   |   | 3 | more than 99 |
| 5* | toluene | 3 | 38 |
|   |   | 24 | 98 |
| 6* | dichloromethane | 2 | 34 |
|   |   | 18 | 46 |
| 7* | o-dichlorobenzene | 2 | 59 |
|   |   | 18 | 72 |
| 8* | diethyl ether | 3 | 54 |
|   |   | 20 | 91 |
| 9* | diisobutyl ketone | 20 | 80 |
| 10* | nitromethane | 5 | 5 |
|   |   | 21 | 13 |
| 11* | 1,4-dioxane | 18 | 0 |
| 12* | N,N-dimethylform-amide | 5 | 5 |
|   |   | 21 | 7 |
| 13* | dimethylsulph-oxide | 2 | 1 |
|   |   | 18 | 0 |

*) not according to the invention

EXAMPLE 3

Preparation of α-cyano 3-phenoxybenzyl 2-(4-chlorophenyl)-3-methylbutanoate

A 50 ml round-bottomed flask equipped with a magnetic stirrer was charged with 10 mmol of 3-phenoxybenzaldehyde, 10 mmol of 2-(4-chlorophenyl)-3-methylbutanoyl chloride, 12 mmol of sodium cyanide and 20 ml of n-heptane and the mixture thus formed was stirred. Five experiments were carried out in this manner, see Table III.

TABLE III

| 1 | 2 | 3 | 4 | 5 | 6 |
|---|---|---|---|---|---|
| Exp. no. | Water added ml | Molar ratio water to NaCN | Reaction time, h | Yield ester, % | Deviating conditions |
| 1 | — | 0.012* | 2 | 91 | |
|   |   |   | 18 | 100 | |
| 2 | 0.02 | 0.105* | 0.5 | 89 | |
|   |   |   | 1.0 | 100 | |
| 3 | 1.0 | 4.64 | 3 | 86 | |
|   |   |   | 18 | more than 99 | |
| 4 | 1.0 | 4.64 | 3 | 61 | carried out at 60° C |
|   |   |   | 19 | 98 | |
| 5 | 0.02 | 0.105* | 1 | 94 | 10.5 mmol of NaCN was used. |
|   |   |   | 3 | more than 99 | |

*solid NaCN was present

Column 1 in Table III states the number of the experiment, column 2 the amount of water, if any, added to the starting mixture (excluding the water present in the sodium cyanide), column 3 the molar ratio of water to sodium cyanide and column 4 the reaction time. The yield of the desired ester is presented in column 5. Conditions different from those stated above are mentioned in column 6. The ester separated as a pale yellow oil during the reaction but redissolved on warming to a temperature between 40° and 50° C.

The warm reaction mixture of experiment 1 was filtered and the n-heptane was flashed from the filtrate to give the ester as a pale yellow oil in quantitative yield.

The reaction mixture obtained in experiment 2 was warmed up to a temperature of 40°–45° C and filtered. The n-heptane was flashed from the filtrate to obtain the ester in quantitative yield as a pale yellow oil with a purity of 98%.

The reaction mixture obtained in experiment 3 was mixed with 5 ml of water to dissolve the precipitated sodium chloride. The mixture was allowed to settle out and the water layer was separated. The heptane layer was washed twice with 20 ml of a 1 M aqueous sodium bicarbonate solution and once with 20 ml of water. The washed liquid was dried and n-heptane was flashed from the dried liquid to give the ester in a yield of 97%.

EXAMPLE 4

Preparation of five esters

A 50 ml round-bottomed flask equipped with a magnetic stirrer was charged with 10 mmol of an aromatic aldehyde, 10 mmol of a (cyclo)aliphatic acyl chloride, 12 mmol of sodium cyanide, 0.02 ml of water and 20 ml of n-heptane. The molar ratio of water to sodium cyanide was 0.105, solid NaCN being present. The mixture thus formed was stirred and analysed.

Five experiments were conducted in this manner, see Table IV, experiments 1–5. Column 1 states the number of the experiment, column 2 the aromatic aldehyde used, column 3 the (cyclo)aliphatic acyl chloride used, column 4 the reaction time, column 5 the ester formed and column 6 presents the yield of this ester.

TABLE IV

| 1 | 2 | 3 | 4 | 5 | 6 |
|---|---|---|---|---|---|
| Exp. no. | Aldehyde | Acyl chloride | Reaction time, h | Ester formed | Yield of ester, % |
| 1 | Benzaldehyde | Acetyl chloride | 3 | α-cyanobenzyl acetate | 14 |
|   |   |   | 22 |   | 38 |
| 2 | " | 2-methylpropanoyl chloride | 1 | αcyanobenzyl isobutyrate | 96 |
|   |   |   | 2 |   | 99 |
| 3 | " | 2-(4-chlorophenyl)-phenyl)-3-methyl-butanoyl chloride | 1 | α-cyanobenzyl 2-(4-chlorophenyl)-3-methylbutanoate | 97 |
|   |   |   | 2 |   | 100 |
| 4 | " | 2,2,3,3-tetramethyl-cyclopropanecarbonyl chloride | 2 | α-cyanobenzyl 2,2,3,3-tetra-methylcyclopropane-carboxylate | 52 |
|   |   |   | 5 |   | 81 |

TABLE IV-continued

| Exp. no. | Aldehyde | Acyl chloride | Reaction time, h | Ester formed | Yield of ester, % |
|---|---|---|---|---|---|
|  |  |  | 21 |  | 91 |
| 5 | 3-phenoxybenzaldehyde | 2-(2,2-dichlorovinyl)-3,3-dimethylcyclopropanecarbonyl chloride | 1 | α-cyano-3-phenoxy benzyl 2-(2,2-dichlorovinyl)-3,3-dimethylcyclopropanecarboxylate | 43 |
|  |  |  | 18 | 100 |  |
| 6 | " | " | 3 | " | 49 |
|  |  |  | 21 |  | 94 |
|  |  |  | 44 |  | 99 |

The reaction mixture obtained in experiment 5 was warmed to a temperature between 40° and 50° C to dissolve the pale yellow oil separated, and then filtered. n-Heptane was flashed from the filtrate to give the ester as a pale yellow oil in quantitative yield.

Experiment 6 was a repetition of experiment 5 with the difference that 1.00 ml instead of 0.02 ml of water was added, the sodium cyanide being completely dissolved in the aqueous phase and the molar ratio of water to sodium cyanide being 4.64, and that 10.2 mmol of the acyl chloride was used.

Example 5

Preparation of α-cyano-3-phenoxybenzyl 2-(2,2-dichlorovinyl)-3,3-dimethylcyclopropanecarboxylate A 50 ml round-bottomed flask equipped with a magnetic stirrer was charged with 10 mmol of 3-phenoxybenzaldehyde, 2-2,3-dichlorovinyl)-3,3-dimethylcyclopropanecarbonyl chloride, 12 mmol of sodium cyanide, water and 20 ml of n-heptane. The mixture thus formed was stirred and analysed. Two experiments were carried out in this manner, see Table V, which states how much acyl chloride and water was added and also presents the yield of the ester wanted.

The reaction mixture obtained in experiment 2 was warmed to a temperature between 40° and 50° C and filtered. The filtrate was washed twice with 20 ml of a 1 M aqueous sodium bicarbonate solution, once with 20 ml of water, dried and n-heptane was flashed from the filtrate to give the ester as a pale yellow oil.

TABLE V

| Exp. No. | Acyl chloride mmol | Water added ml | Molar ratio water to NaCN | Reaction time, h | Yield of ester, % |
|---|---|---|---|---|---|
| 1 | 10.0 | 0.02[1] | 0.105 | 1 | 43 |
|  |  |  |  | 18 | 100 |
| 2 | 10.2 | 1.00 | 4.64 | 3 | 49 |
|  |  |  |  | 21 | 94 |
|  |  |  |  | 44 | 99 |

[1] solid NaCN was present.

EXAMPLE 6

Preparation of α-cyano-3-phenoxybenzyl 2-(4-chlorophenyl)-3-methylbutanoate on an enlarged scale A 500 ml round-bottomed flask equipped with a paddle stirrer was charged with 100 mmol of 3-phenoxybenzaldehyde, 100 mmol of 2-(4-chlorophenyl)-3-methylbutanoyl chloride, 120 mmol of sodium cyanide, 10 ml of water, and 200 ml of n-heptane. The molar ratio of water to sodium cyanide was 4.64, all NaCN being dissolved. The mixture thus formed was stirred and analysed. Table VI presents the yields and purities of the desired ester after the reaction time indicated.

TABLE VI

| Exp. No. | Reaction time, h | Yield of ester, % | Purity of ester, % |
|---|---|---|---|
| 1 | 45 | 99 | 96 |

The reaction mixture obtained in experiment 1 was warmed to a temperature between 40° and 50° C and filtered. The filtrate was washed twice with 50 ml of a 1 M aqueous sodium bicarbonate solution, once with 50 ml of water, dried and n-heptane was flashed from the dried solution to give the desired ester.

EXAMPLE 7

Preparation of α-cyano-3-phenoxybenzyl 2-(4-chlorophenyl)-3-methylbutanoate on an enlarged scale in the presence of solid cyanide A 500 ml round-bottomed flask equipped with a paddle stirrer was charged with 100 mmol of 3-phenoxybenzaldehyde, 100 mmol of 2-(4-chlorophenyl)-3-methylbutanoyl chloride, 120 mmol of sodium cyanide, 0.2 ml of water, and 200 ml of n-heptane. The molar ratio of water to sodium cyanide was 0.105, solid NaCN being present. After stirring for four hours the mixture was warmed to a temperature between 40° and 50° C and filtered. n-Heptane was flashed from the filtrate to leave the desired ester in quantative yield and a purity of 97%.

EXAMPLE 8

Preparation of α-cyano-3-phenoxybenzyl 2,2,3,3-tetramethylcyclopropanecarboxylate using two methods Methods A and B were applied to prepare the ester wanted. Method A - A 50 ml round-bottomed flask equipped with a magnetic stirrer was charged with 10 mmol of 3-phenoxybenzaldehyde, 10 mmol of 2,2,3,3-tetramethylcyclopropanecarbonyl chloride, 12 mmol of sodium cyanide, 1.00 ml of water, and 20 ml of n-heptane. The molar ratio of water to NaCN was 4.64, all NaCN being dissolved. The mixture thus formed was stirred for 1.5 hours and analyzed. Method B - The flask used for method A was charged with 10 mmol of 3-phenoxybenzaldehyde, 12 mmol of sodium cyanide, 10 ml of n-heptane, 1.00 ml of water, the molar ratio of water to NaCN being 4.64. An amount of 10 mmol of 2,2,3,3-tetramethylcycloproanecarbonyl chloride dissolved in 10 ml of n-heptane was introduced into the flask during a period of 70-75 min. The yield of the ester was determined at the end of this period.

Table VII presents the yield of the desired ester.

TABLE VII

| Exp. no | Yield of ester, %, | |
|---|---|---|
| | Method A | Method B |
| 1 | 17 | 40 |

What is claimed is:

1. A process for the preparation of an ester of formula I

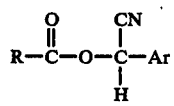

wherein Ar is a phenoxy substituted phenyl group and R is a branched-chain alkyl group substituted by a halophenyl group, which process comprises contacting an aromatic aldehyde of the formula ArC(O)H and an acyl halide of the formula RC(O)Hal, in which formulas Ar and R have the same meaning as in formula I and Hal represents a halogen atom having an atomic number of from 9 to 53, inclusive, with water and water-soluble cyanide in the presence of at least one substantially water-immiscible alkane solvent containing from 6 to 10 carbon atoms or mixture thereof and recovering the desired ester product from the reaction mixture.

2. A process according to claim 1, in which the alkane is n-heptane.

3. A process according to claim 1 in which the total amount of the water-soluble cyanide is dissolved in the water.

4. A process according to claim 1, which is conducted at a temperature in the range of from 10° C to 50° C.

5. A process according to claim 1, in which the water-soluble cyanide is sodium cyanide.

6. A process according to claim 1, in which the molar ratio of the amount of acyl halide of the formula RC(O)Hal to the amount of the aromatic aldehyde of the formula ArC(O)H is in the range of from 1.1 to 1.0.

7. A process according to claim 6, in which the molar ratio of the amount of acyl halide to the amount of aldehyde is 1.0.

8. A process according to claim 1, in which Hal in the formula RC(O)Hal represents a chlorine atom.

9. A process according to claim 1 in which the group R in the general formula RC(O)Hal is an alkyl group having a tertiary or quaternary carbon atom bound to the group —C(O)Hal.

10. A process according to claim 9, in which the group R is a 1-(4-chlorphenyl)-2-methylpropyl group.

11. A process according to claim 10, which is carried out by forming a mixture of the total amounts of the aromatic aldehyde, the acyl halide, the water, the water-soluble cyanide and the alkane, and stirring of the mixture thus formed.

12. A process according to claim 2 which is conducted at a temperature in the range of from 10° C to 50° C using sodium cyanide dissolved in water as the water-soluble cyanide and a molar ratio of acyl halide of the formula RC(O)Hal to the amount of the aromatic aldehyde of the formula ArC(O)H is in the range of from 1.1 to 1.0.

13. A process according to claim 12 wherein the ester of formula I is α-cyano-3-phenoxybenzyl 2-(4-chlorophenyl)-3-methylbutanoate.

* * * * *